(12) United States Patent
Keles

(10) Patent No.: US 7,074,036 B1
(45) Date of Patent: Jul. 11, 2006

(54) PALATAL EXPANSION DEVICE AND METHODS

(76) Inventor: Ahmet Ozlem Keles, 154 Newbury St., Apt.3AF, Boston, MA (US) 02116

( * ) Notice: Subject to any disclaimer, the term of this patent is extended or adjusted under 35 U.S.C. 154(b) by 0 days.

(21) Appl. No.: 10/908,536

(22) Filed: May 16, 2005

(51) Int. Cl.
*A61C 3/00* (2006.01)

(52) U.S. Cl. ............................................ 433/7

(58) Field of Classification Search .................. 433/7
See application file for complete search history.

(56) References Cited

U.S. PATENT DOCUMENTS

| | | | |
|---|---|---|---|
| 3,835,540 A | | 9/1974 | Biederman |
| 4,571,177 A | | 2/1986 | Dahan |
| 4,917,601 A | | 4/1990 | Williams |
| 5,281,133 A | * | 1/1994 | Farzin-Nia ........... 433/7 |
| 5,472,344 A | | 12/1995 | Binder et al. |
| 5,975,894 A | | 11/1999 | Pozzi |
| 6,139,316 A | * | 10/2000 | Sachdeva et al. ........ 433/7 |
| 6,626,665 B1 | | 9/2003 | Keles |
| 2003/0207225 A1 | * | 11/2003 | Huge et al. ............. 433/7 |

OTHER PUBLICATIONS

OrthoXpand, International Inc. Brochure, 2nd Generation RatchetRax (2004).
OrthodonticProducts, Product Catalog, Novicom, Inc, pp. 35, (Jun. 2005).
OrthodonticProducts, Buyer's Guide 2005, Novicom, Inc, pp. 16-17, (Dec. 2004/Jan. 2005).
Biederman W.A., *J Pract Orthod*, Hygienic Appliance for Rapid Expansion 2:67-70 (1968).
Haas A.J., *Angle Orthod*, Rapid Expansion of the Maxillary Dental Arch and Nasal Cavity by Opening the Midpalatal Suture, 31:73-90 (1961).
Haas, A. J., *Am. J. of Orthodontics*, 57(3):219-255 (1970).
Wertz R.A., *Am J Orthod*, Skeletal and dental changes accompanying rapid midpalatal suture opening, 58:41-66 (1970).
Haas, A.J., *Angle Orthod*. The Treatment of Maxillary Deficiency by Opening the Midpalatal Suture;35:200-17 (1965).

* cited by examiner

*Primary Examiner*—Cary E. O'Connor
(74) *Attorney, Agent, or Firm*—Antoinette G Giugliano PC

(57) ABSTRACT

The present invention relates to a palatal expansion device that has a screw having one or more activation arms wherein the screw connects two blocks, each block having an opening for receiving the screw; a stabilizer attached to the blocks; and a spring extension positioned opposite the activation arms, wherein the spring extension is attached to the stabilizer. The present invention involves methods for expanding the maxillary arch, and kits including the device.

17 Claims, 3 Drawing Sheets

PALATAL EXPANSION DEVICE AND METHODS

BACKGROUND OF THE INVENTION

Constricted maxillary arch is often a significant dental and skeletal problem in field of orthodontics. Prior to the present invention, a fixed palatal expansion device generally consisted of a 4-band device with a midpalatal screw. In this example, the appliance had fixed bands on the maxillary first permanent molars and first premolars, connected on each side by a rigid bar, with both sides connected to each other by the screw. Such an appliance often consisted of 2 stabilizing bars, a screw with a hole in the middle for activation, and 2 metal blocks. These metal blocks are connected with each other by the screw and upon activation the blocks move apart from each other to achieve the transverse expansion of the upper jaw. In most instances, activation of the screw is performed by a pin shaped key. The appliance is initially cemented to the teeth and activated twice a day by the patient with the key until the desired expansion is achieved.

Looking at the above-described device from a clinical point of view, patients have a hard time finding the hole on the screw with the pin shaped key, inserting the key and turning the screw backwards in the direction of the throat by looking to an inverted image on a mirror. The hole on the screw is often very small; generally its diameter is less than a millimeter. Hence, even with the help of the pin shaped key, it is difficult to find. Furthermore, other risks exist. They include injuring the soft palate during insertion of the key and/or swallowing the key during activation. In some cases, accidental swallowing of orthodontic expansion appliance keys has been reported.

After the desired expansion is achieved, the activation of the screw is stopped and the appliance is maintained in the mouth for 3 months for stabilization and adaptation of the tissues. However during this time period, unwinding of the screw can happen thereby causing the blocks to retract, and some of the achieved expansion can be lost during the stabilization period.

Hence, a need exists for an effective palatal expander that is patient friendly. In particular, a need exists for a palatal expander that does not require a key, that is easy to use, and achieves the desired maxillary expansion without retraction of the device.

SUMMARY OF THE INVENTION

The present invention relates to a palatal expansion device that has a screw having one or more activation arms wherein the screw connects two blocks, each block having an opening for receiving the screw; a stabilizer (e.g., one or more stabilizers) attached to the blocks; and a spring extension positioned opposite the activation arms, wherein the spring extension is attached to the stabilizer. The device further includes two or more retaining wires (e.g., four wires) for securing the device to the teeth, wherein the wires are laterally attached to the blocks. In one embodiment, the screw perpendicularly transects the blocks at the opening. The spring extension is made from an alloy (e.g., nickel titanium alloy), a metal, a plastic, or rubber.

In another embodiment, the present invention pertains to a palatal expansion device that has two blocks; a means for separating the two blocks with one or more activation arms; a means for stabilizing the blocks (e.g., a stabilizer); and a self-locking or anti-wind back mechanism (e.g., a spring extension) that engages the activation arm to thereby prevent retraction of the blocks. The means for stabilizing (e.g., a prism shaped bar, or cylindrical shaped rod) includes, in one embodiment, a rod securely attached to the blocks (e.g., welded, connected by clasps or bands, cemented). The embodiment further includes two or more retaining wires (e.g., four wires) for securing the appliance to teeth, wherein the wires are laterally attached to the blocks.

The present invention also includes methods of expanding a maxillary arch of a person. The methods include the steps of securing palatal expansion device, as described herein and engaging the activation arm to thereby expand the arch. The activation arm can be engaged on a daily basis (e.g., once, twice, or three times a day), every other day, or every few days, depending on the extent of the expansion. The period of activation can be from about 1 week and about 2 weeks, or more (e.g,. about 3 or 4 weeks). The period of activation can be followed by a period of stabilization of between about 2 and about 4 months (e.g. an average of about 3 months).

A kit for palatal expansion is further embodied by the present invention. The kit includes the palatal expansion device described herein and two or more retaining wires (e.g., four wires) for securing the device to teeth. The kit can additionally include additional items normally associated with securing or using such a device.

The present invention has several advantages. The device does not require a pin shaped key for activation of the screw because an activation arm is built-in into the device. The device of the present invention is safer because there is no risk of swallowing a pin shaped key or puncturing the soft palate during insertion of such a key. The built-in activation arm more easily allows for activation of the screw and is therefore more patient friendly. As such, greater patient compliance is obtained. Another advantage of the present invention is the built-in locking (e.g., anti-wind back) mechanism which prevents the screw from winding back after the desired expansion is achieved.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
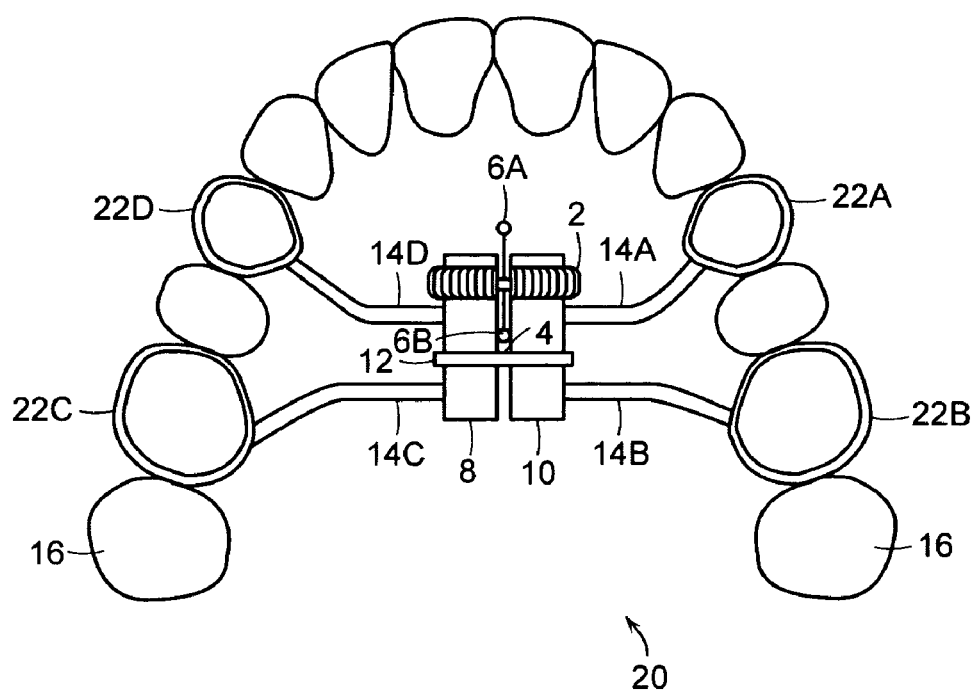
FIG. 1 is a diagram showing an embodiment of the palatal expansion device of the present invention secured to a maxillary arch.

Referring to FIG. 1, palatal expansion device 20 is secured to maxillary arch 16 by bands 22A–22D and retaining wires 14A–14D. Palatal expansion device 20 has a mid-palatal screw 2 that separates blocks 8 and 10 to expand the upper jaw and dentition. In this embodiment, screw 2 has four prong-shaped activation arms, activation arms 6A–6D, that are securely attached to a middle portion of screw 2. A detailed view of screw 2 and activation arms 6A–6D are shown in FIG. 3D. In addition to a screw, other means for separating the block can be use so long as the means is attached to an activation arm that can be engaged by the user and acts to separate the blocks, as described herein. Additionally, a combination of one or more screws can be used in place of a single screw. For example, two screws opposing each other can be used to push the blocks outward, connected by a metal connector to which the activation arms are secured. In one embodiment, turning an activation arm causes screw 2 to turn a ¼of a turn. The number of activation arms and the tread of the screw can be adjusted to obtained the desired expansion distance for each activation. In one embodiment, a 2 mm screw, with 4 activation arms, causes the screw to achieve a 0.25 mm expansion. Similarly, in another embodiment, a screw with a smaller diameter, e.g., a 1 mm screw, with 2 activation arms, could also cause the screw to achieve the same 0.25 mm expansion. The tread of the screw (e.g., the diameter of the screw) can range from between about 0.5 mm and about 4 mm, and the number of activation arms can range from 1 to 8 arms to obtain the desired expansion for each activation, and preferably between 2 and 4 arms. The present invention includes a device that expands, for each activation, between about 0.1 mm to about 0.4 mm, and preferably between about 0.2 mm and about 0.3 mm (e.g., about 0.25 mm).

The device is worn for a period of between about 1 week and about 2 weeks, or more (sometimes about 3 or 4 weeks) to obtain the maximum desired expansion. The device of the present invention can therefore achieve a maximum expansion between about 3 mm and about 15 mm, and preferably between 7 mm and about 11 mm (e.g., about 7 mm, about 9 mm or about 11 mm) The maximum range of expansion can be adjusted by lengthening or shortening the screw, and the stabilizing bars, as further described herein. The screw size can be selected based on the amount of expansion needed.

FIG. 1 shows activation arms 6A–6D having a ball shaped head on the end of each arm to more easily allow the patient to turn it. However, the shape of the end of the activation arm can be of other shapes, so long as the patient can engage the arm to turn it. Preferably, the end of the activation arm is shaped without sharp edges to avoid accidental puncturing by the tongue or finger. The built-in activation arm relinquishes the need for a pin-like key to turn the screw, and all the disadvantages associated with the use of such a key (e.g., trying to place the pin to the small hole of the screw to activate the screw, puncturing the soft palate, accidental swallowing of the key, losing the key, etc.). The embodiment shown in FIG. 1 allows the activation arms and screw to work like a sprocket wheel.

Figure 3E:
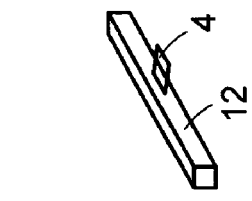
FIG. 3E is a diagram of a perspective view of the spring extension attached to the stabilization bar of an embodiment of the palatal expansion device of the present invention.
Figure 3D:
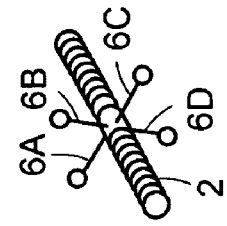
FIG. 3D is a diagram of a perspective view showing the screw and four activation arms attached to the screw for an embodiment of the palatal expansion device of the present invention.
Figure 3C:
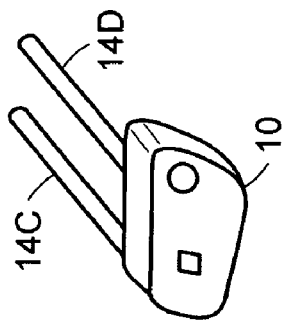
FIG. 3C is a diagram of a perspective view showing the inside of one block, two retaining wires, a square hole for receiving a stabilization bar, and a round hole for receiving the screw for an embodiment of the palatal expansion device of the present invention.

Stabilizing bar 12 along with spring extension 4 are shown in FIG. 1, and in more detail in FIG. 3E. Stabilizing bar 12 is square shaped prism which goes through the square shape holes of blocks 8 and 10. See FIGS. 3A and 3C. One or more stabilizing bars can be used. The holes transect blocks 14A and B to allow for stabilizing bar 12 to slide freely along the blocks during expansion. Stabilizing bar 12 functions to stabilize the device to keep the blocks moving along a straight axis, e.g., by preventing the blocks from swiveling during expansion. Any means for stabilizing the blocks can be used so long as the means keeps the blocks moving along a straight axis and in the direction for expansion. In addition to a bar, stabilizing means can also include a cylindrical shaped rod. The stabilizing bar can be made from metal, plastic, rubber or any other material known in the art or later developed that can withstand the force of expansion.

Figure 3B:
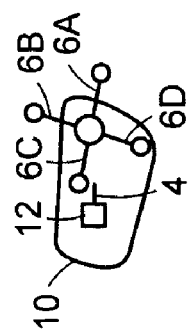
FIG. 3B is a diagram of a side view showing a spring extension attached to the stabilization bar and positioned opposite to four activation arms of an embodiment of the palatal expansion device of the present invention.
Figure 3A:
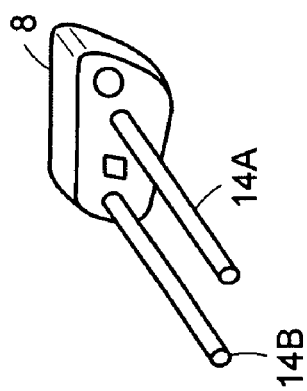
FIG. 3A is a diagram of a perspective view showing the outside of one block, two retaining wires, a square hole for receiving a stabilization bar, and a round hole for receiving the screw for one embodiment of the palatal expansion device of the present invention.

Attached to stabilizing bar 12 is spring extension 4. Spring extension 4 acts as a self-locking mechanism for screw 2. FIGS. 1, 3B and 3E show spring extension 4 that looks like a plate projection that functions like a cog to lock the screw. Spring extension 4 prevents screw 2 from winding back, which in turn prevents retraction of the blocks. A spring extension allows the activation arm to pass in one direction (e.g., from bottom to top), but does not allow for the activation arm to reverse direction (e.g., from top to bottom) to prevent wind back of the screw. A spring extension can be positioned perpendicularly to stabilizing bar 12, or at an angle (e.g., a slightly downward angle) to achieve unidirectional directional flow. The spring extension can also have a rounded or cup-like shape, or other shape that complements the end of the activation arm. In addition to a spring extension, other self locking means (e.g., anti-wind back means) can be used to prevent the activation arms from winding back. The spring extension can be made from metal, alloy (e.g., nickel titanium alloy), plastic, rubber, or other suitable material that is known in the art or later developed.

Blocks 8 and 10 act as supports for device 20. Such blocks can be made from metal, rubber, plastic or any other suitable material known in the art or later developed to act as supports for the expansion device of the present invention. Blocks 8 and 10 have an opening to receive screw 2. The opening used to receive screw 2 can extend along the entire width of one or both blocks. For example, in FIGS. 3A and C, the opening that receives screw 2 extends along the entire width of both blocks to allow screw 2 to extend past the end of each block. In this embodiment, both blocks move along the screw during expansion. In another embodiment, one block can have a screw opening that extends along the entire width of the screw, while the other block has a screw mounted to the block. During expansion, only one block, instead of two, moves along the screw, which in turn allows an equal expansion.

As shown in FIG. 1, blocks 8 and 10 also have an opening for receiving stabilization bar 12. The opening allows blocks 8 and 10 to slide along stabilization bar 12, as described herein. Additionally in the embodiment shown in FIGS. 1, 3A and 3C, blocks 8 and 10 accommodate retaining wires 14A–D. The device of the present invention can have two or more retaining wires, and preferably four retaining wires. Retaining wires are used to secure the device to the maxillary arch. In one example, retaining wires can be secured to the molar and premolar bands. They project from the outside surfaces of the blocks and extend outward toward the molar and premolar bands.

Figure 2:
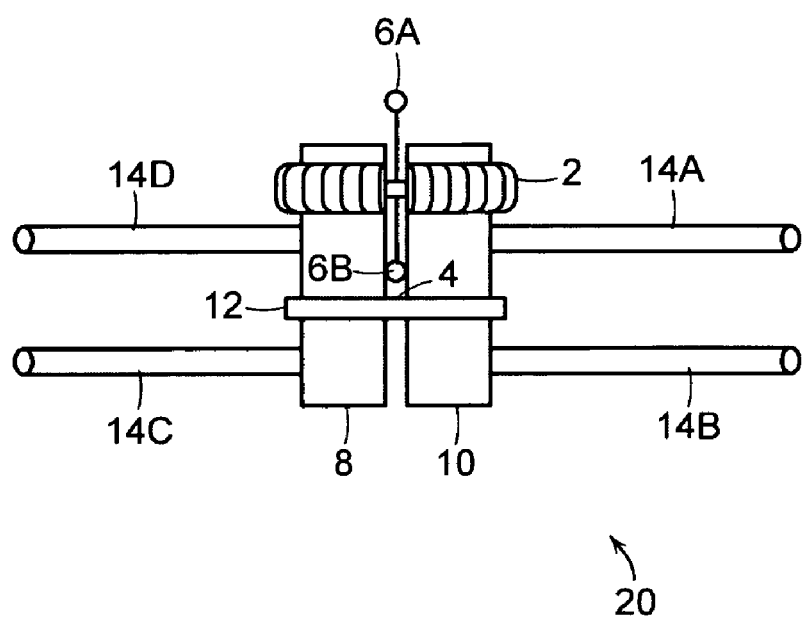
FIG. 2 is a diagram of a top view of another embodiment of the palatal expansion device of the present invention.

FIG. 2 shows device 20 when it is not secured to the maxillary arch. Retaining wires 14A–D are straight and can be soldered to the premolar and molar band, or bonded directly to the palatal side of the molar and premolar teeth. FIG. 2 shows one embodiment of the palatal expansion device of the present invention prior to being secured to a patient. The device can be provided with or without retaining wires. In the case where the device is not provided with retaining wires, the device has a point of attachment for the wires that can be threaded or attached by the orthodontist in the dental office.

The present invention also includes methods for expanding the maxillary arch. The steps of the method includes securing the device, as described herein, to the maxillary arch (e.g., to the molar and premolar bands), and engaging the activation arms (e.g., turning the activation arm). In general, palatal expansion therapy affects craniofacial structures and the teeth onto which the appliance is adapted. In the horizontal plane, the midpalatal suture separates asymmetrically in a "V"-shaped pattern, with the greatest expansion occurring in the anterior aspect of the palate. Data indicates that the greatest resistance to sutural splitting is in the posterior aspect of the palate, because of the articulation of the maxilla with the surrounding cranial bones, such as the zygomatic buttress. These anatomic considerations result in the above-mentioned pattern of expansion with any tooth-borne appliance. Therefore, in one embodiment the device is placed near the sources of anatomic resistance such as the zygomatic buttresses. Such placement causes a more uniform pattern of palatal expansion.

As described herein, the methods of the present invention include activation that occurs on a daily basis (e.g., once a day, twice a day, or three times a day), every other day, several times a week. In one example, activation occurs twice a day by turning the activation arm downward and backward wherein every activation is 0.25 mm. The patient can activate the device with the help of the index finger until it clicks. At the time that the arm clicks, the activation arm disappears and hides between the metal blocks and does not irritate the tongue. The activation occurs until the desired expansion is obtained, e.g., between about 7 mm and about 11 mm. In one aspect of the invention, the period for expansion is between about 1 and about 2 weeks. The expansion period can be followed by a stabilization period (e.g. about 3 months), where the maxillary arch acclimates to the expansion. The spring extension prevents the screw from unwinding and maintains the expansion.

The present invention also relates to a kit including the device, as described herein, and two or more retaining wires. Optionally any other tool or items used to secure the device to the maxillary arch or activate the device can also be included.

EXEMPLIFICATION

The palatal expansion device shown in FIG. 1 can be made with the following specifications. The device can be made with 2 metal blocks and a metal screw having a tread of 2 mm, and a length of either 7 mm, 9 mm or 11 mm. Each metal block has an opening to receive and complement the screw, and the opening runs the entire length of the screw. The screw has 4 activation arms attached to the center, each arm positioned to cause the screw to turn a ¼ of a turn. Each activation arm has a ball-like protections at its end. The screw of the device together with the activation arms work like a sprocket wheel. The device can be made for activation that occurs twice a day, with every activation being 0.25 mm. The device also has a stabilizing bar which is a square shaped prism that goes through the square shape holes of the blocks. Attached to the stabilization bar is a spring extension that acts as a self-locking or anti-wind back mechanism for screw. The spring extension, that can made from a nickel titanium allow, looks like a plate projection that functions like a cog to lock the screw. The device has 4 retaining metal wires, wherein 2 wires are attached to each metal block.

A patient wearing the device can activate it using the index finger until it clicks. At the time that the arm clicks, the activation arm disappears and hides between the metal blocks and does not irritate the tongue. The period for expansion is between about 1 and about 2 weeks. If further expansion is needed, a second, longer screw can be used for a period of about 1 to about 2 additional weeks (e.g., about 3 or 4 weeks total). The expansion period is often followed by a stabilization period (e.g. about 3 months), where the maxillary arch acclimates to the expansion.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A palatal expansion device that comprises:
   a. a screw having one or more built-in activation arms wherein the screw connects two blocks, each block having an opening for receiving the screw;
   b. one or more stabilizers attached to the blocks; and
   c. a spring extension positioned opposite the activation arms, wherein the spring extension is attached to the stabilizer,
wherein the built-in activation arm is engaged by the spring extension to thereby prevent retraction of said blocks.

2. The palatal expansion device of claim 1, further including two or more retaining wires for securing the appliance to teeth, said wires are laterally attached to said blocks.

3. The palatal expansion device of claim 2, wherein four retaining wires are attached to said blocks.

4. The palatal expansion device of claim 1, wherein the screw perpendicularly transects said blocks at the opening.

5. The palatal expansion device of claim 1, wherein the spring extension is made from an alloy, a metal, a plastic, or rubber.

6. The palatal expansion device of claim 5, wherein the spring extension is made from a nickel titanium alloy.

7. A palatal expansion device that comprises:
   a. two blocks:
   b. a means for separating the two blocks with one or more activation arms;
   c. a means for stabilizing said blocks; and
   d. a self-locking mechanism that engages the activation arm to thereby prevent retraction of said blocks.

8. The palatal expansion device of claim 7, wherein the means for separating said blocks includes a screw.

9. The palatal expansion device of claim 7, wherein the means for stabilizing comprises a bar or a rod securely attached to said blocks.

10. The palatal expansion device of claim 7, wherein the self-locking mechanism comprises a spring extension.

11. The palatal expansion device of claim 7, further including two or more retaining wires for securing the appliance to teeth, said wires are laterally attached to said blocks.

12. A method of expanding a maxillary arch of a person, said method comprises the steps of:
 a. securing palatal expansion device in the maxillary arch of said person, wherein the device comprises:
  i. a screw having one or more built-in activation arms wherein the screw connects two blocks, each block having an opening for receiving the screw;
  ii. a stabilizer attached to the blocks; and
  iii. a spring extension positioned opposite to the activation arms, wherein the spring extension is attached to the stabilizer, and wherein the built-in activation arm is engaged by the spring extension to thereby prevent retraction of said blocks; and
 b. engaging the activation arm to thereby expand the arch.

13. The method of claim 12, further including engaging the activation arm daily.

14. The method of claim 12, wherein the activation arm is engaged daily for a period of between about 1 week and about 2 weeks.

15. A kit for palatal expansion that comprises:
 a. palatal expansion device having:
  i. a screw having one or more built-in activation arms wherein the screw connects two blocks, each block having an opening for receiving the screw;
  ii. a stabilizer attached to the blocks; and
  iii. a spring extension positioned opposite to the activation arms, wherein the spring extension is attached to the stabilizer, and wherein the built-in activation arm is engaged by the spring extension to thereby prevent retraction of said blocks; and
 b. two or more retaining wires for securing the appliance to teeth, said wires are laterally attached to said blocks.

16. The kit of claim 15, further including four retaining wires.

17. The kit of claim 15, further including additional tools or items used to secure said device.

* * * * *